US011992454B2

(12) United States Patent
Izumi

(10) Patent No.: US 11,992,454 B2
(45) Date of Patent: May 28, 2024

(54) MOVEMENT SUPPORT SYSTEM, TOOL AND METHOD FOR PHYSICALLY DISABLED PERSON

(71) Applicant: NEC Corporation, Tokyo (JP)

(72) Inventor: Tomofumi Izumi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 308 days.

(21) Appl. No.: 17/603,379

(22) PCT Filed: Apr. 22, 2020

(86) PCT No.: PCT/JP2020/017351
§ 371 (c)(1),
(2) Date: Oct. 13, 2021

(87) PCT Pub. No.: WO2020/218349
PCT Pub. Date: Oct. 29, 2020

(65) Prior Publication Data
US 2022/0175610 A1   Jun. 9, 2022

(30) Foreign Application Priority Data
Apr. 23, 2019   (JP) ................................. 2019-081812

(51) Int. Cl.
*A61H 3/06*   (2006.01)
*G01C 21/20*   (2006.01)

(52) U.S. Cl.
CPC ............. *A61H 3/066* (2013.01); *A61H 3/061* (2013.01); *A61H 3/068* (2013.01); *G01C 21/206* (2013.01); *A61H 2003/063* (2013.01); *A61H 2003/065* (2013.01); *A61H 2201/5048* (2013.01); *A61H 2201/5097* (2013.01)

(58) Field of Classification Search
CPC ........... A61F 9/08; A61G 5/1051; A61H 3/06; A61H 3/061; A61H 3/066; A61H 3/068;
(Continued)

(56) References Cited

U.S. PATENT DOCUMENTS

| 2007/0096908 A1* | 5/2007 | Chu | G09B 21/008 340/572.1 |
| 2009/0132158 A1* | 5/2009 | Sironi | G01S 13/76 701/532 |
| 2018/0017393 A1* | 1/2018 | Willson | A61H 3/066 |

FOREIGN PATENT DOCUMENTS

| JP | H08-006489 A | 1/1996 |
| JP | H08-246422 A | 9/1996 |

(Continued)

OTHER PUBLICATIONS

International Search Report for PCT Application No. PCT/JP2020/017351, dated Jul. 14, 2020.
(Continued)

*Primary Examiner* — Stephen R Burgdorf

(57) ABSTRACT

A movement support system for a physically disabled person comprises: movement support tool; a plurality of passage units; and control apparatus. The movement support tool comprises: magnetically attractive part; non-contact tag part; reception part; input part; output part; and control part. The passage unit comprises: electromagnet part, non-contact reading part, transmission part, and control part. The control apparatus acquires the destination information and the user ID from the movement support tool; acquires the user ID and the position information from the first passage unit closest to the movement support tool; and calculates route from the position information to the destination information; generates guidance based on the route and position information; outputs the generated guidance from the movement support tool; and controls each of the electromagnet part of the plurality of passage units so as to attract (pull) the magnetically attractive part in traveling direction of the route.

20 Claims, 10 Drawing Sheets

(58) Field of Classification Search
CPC ........ A61H 2003/063; A61H 2003/065; A61H 2201/1659; A61H 2201/169; A61H 2201/5048; A61H 2201/5097; A63B 24/0087; B25J 9/0003; B25J 11/008; G01C 21/20; G01C 21/206; G01C 21/26; G05D 1/02; G06F 21/32; G08G 1/005; G08G 1/096811; G08G 1/0969; G09B 21/00
USPC ...................................................... 340/407.1
See application file for complete search history.

(56) References Cited

FOREIGN PATENT DOCUMENTS

| JP | 2000175957 A | * | 6/2000 | ............... A61H 3/06 |
|---|---|---|---|---|
| JP | 2002-235308 A | | 8/2002 | |
| JP | 2003-070514 A | | 3/2003 | |
| JP | 3679388 B2 | * | 8/2005 | ............... A61H 3/06 |
| JP | 2006061587 A | * | 3/2006 | ............... A61H 3/06 |
| JP | 2006-314384 A | | 11/2006 | |
| JP | 2007-172032 A | | 7/2007 | |
| JP | 2013-044135 A | | 3/2013 | |
| TR | 201514429 A | * | 3/2016 | ............... A61H 3/06 |

OTHER PUBLICATIONS

"ShikAI—Station Navigation System for the Visually Impaired", 2018, https://www.progresstech.jp/shikai/.
Kei Sato et al., "Development and Demonstration Experiment of PULL DOG of Navigation System for Visually Impaired Person Using RFID and Quasi-Zenith Satellite", Proceedings of 78th National Convention, Mar. 10, 2016, https://ipsj.ixsq.nii.ac.jp/ej/index.php?active_action=repository_view_main_item_detail&page_id=13&block_id=8&item_id=163034&item_no=1.

* cited by examiner

MOVEMENT SUPPORT SYSTEM, TOOL AND METHOD FOR PHYSICALLY DISABLED PERSON

This application is a National Stage Entry of PCT/JP2020/017351 filed on Apr. 22, 2020, which claims priority from Japanese Patent Application 2019-081812 filed on Apr. 23, 2019, the contents of all of which are incorporated herein by reference, in their entirety.

FIELD

Description of Related Application

The present invention is based on claiming priority of Japanese patent application No. 2019-081812 (filed on Apr. 23, 2019), and the entire contents of the present application shall be incorporated and stated in the present application by reference thereto.

The present invention relates to a movement support system, a tool and a method for a physically disabled person.

BACKGROUND

As a method of supporting (guidance, assisting) the movement (for example, walking) of a physically disabled person (for example, a visually impaired person), a method of inducing walking by braille blocks with protrusions on a surface so that the visually impaired person can recognize it by a tactile sensation of sole of foot, is common. Since an area where the braille blocks are installed is limited and information that can be obtained from the braille blocks is also minimum necessary information for safely guiding, a method that replaces the braille blocks is desired.

In order to guide walking of a visually impaired person, it is necessary to use a position recognizing means (position information acquisition means). For example, in Patent Literature (PTL) 1, a system is disclosed, wherein the system informs information such as a route, a dangerous place, a branch point, and a destination guidance, of a user by voice message, using an RFID (Radio Frequency IDentifier) tag built in a block as the position recognizing means, based on information read from the RFID tag.

Also, in PTL 2, a method is disclosed, wherein the method can go toward a desired direction by recognizing a magnetic force, using a magnet embedded in an upper part of a block as the position recognizing means, when a user wearing shoes having a magnet plate inserted inside passes the upper part of the block.

Further, in Non-Patent Literature (NPL) 1, a system is disclosed, wherein the system derives an accurate travel route from a current location to a destination and navigates to the destination by voice, using a QR (Quick Response) code (registered trademark) displayed on a braille block as the position recognizing means, by reading the QR code (registered trademark) due to a camera of a smartphone executing a dedicated application.

Furthermore, in NPL 2, a system is disclosed, wherein the system guides according to a destination by voice or vibration, using a RFID and a quasi-zenith satellite system (QZSS) as the position recognizing means, when detecting that a user is approaching the destination by the RFID and the quasi-zenith satellite system.
[PTL 1] JP2007-172032A1
[PTL 2] JP2002-235308A1
[NPL 1] "Navigation system for the visually impaired person, shikAI", 2018, https://www.progresstech.jp/shikai/
[NPL 2] Kei Sato et al., "Development and Demonstration Experiment of PULL DOG of Navigation System for Visually Impaired Person Using RFID and Quasi-Zenith Satellite", Proceedings of 78th National Convention, Mar. 10, 2016, https://ipsj.ixsq.nii.ac.j p/ej/index.php?active_action=repository_view_main_item_detail&page_id=13&block_id=8&item_id=163034&item_no=1

SUMMARY

The following analysis is given by the inventors of the present application.

However, if an RFID built into a block such as PTL 1 is used or a QR code (registered trademark) displayed on a braille block such as NPL 2 is used, the time and effort to place the position recognizing means within a reading range has an effect, thereby, it is not possible to give as much walking speed as a guide dog. Also, if using a QR code (registered trademark) or an RFID tag, only static information registered in advance at an embedded point can be notified to a terminal side.

Also, if using a quasi-zenith satellite system or GPS (Global Positioning System) such as NPL 2, since a positioning error affects, it is not possible to obtain a walking speed as much as that of a guide dog.

Further, virtual attraction (pull) by positioning such as PTL 1 and NPLs 1 and 2 may be sensuous essentially, and individual differences occur, and there is a possibility that it is not possible to guide to a destination as an attraction (pull) distance becomes longer.

Furthermore, if using a magnet such as PTL 2, since the magnet is simply embedded in the upper part of the block, it is only possible to recognize that the place is at a braille block. Also, since the magnet embedded in the upper part of the block always generates a magnetic force, a traveling direction can not be specified and an attraction (pull) to the traveling direction can not be performed.

It is a main object of the present invention to provide a movement support system, a tool and a method for a physically disabled person, that it is possible to contribute to navigating a physically disabled person to a destination safely, quickly and without stalling.

A movement support system for a physically disabled person according to a first aspect is a movement support system that comprises: a movement support tool configured to support movement of a user in a passage; a plurality of passage units configured to be arranged side by side in the passage and operate to act on the movement support tool: and a control apparatus configured to be able to communicate with the movement support tool and control operations of the plurality of passage units. The movement support tool comprises: a magnetically attractive part configured to be attracted to a magnet; a non-contact tag part configured so that a user ID is embedded; a reception part configured to receive a wireless signal; an input part configured to be able to input destination information; an output part configured to be able to output a guidance; and a control part configured to control the reception part, the input part, and the output part. The passage units comprise: an electromagnet part configured to be able to attract the magnetically attractive part; a non-contact reading part configured to be able to read the user ID from the non-contact tag part; a transmission part configured to be able to transmit the wireless signal to the reception part; and a control part configured to control the electromagnet part, the non-contact reading part and the transmission part. The control apparatus is configured to execute processings of: acquiring the destination information and the user ID from the movement support tool; acquiring the user ID of the non-contact tag part read by the non-contact reading part of a first passage unit closest to the movement support tool among the plurality of passage units, and preset position information of the first passage unit, from the first passage unit; calculating a route from the position information of the first passage unit to the destination information; generating a guidance based on the route and the preset position information of the first passage unit related to the non-contact reading part that read the user ID of the non-contact tag part of the movement support tool; outputting the generated guidance from the output part of the movement support tool through the transmission part of the first passage unit and the reception part of the movement support tool; and controlling each of the electromagnet parts of the plurality of passage units so as to attract (pull) the magnetically attractive part in a traveling direction of the route based on the route and the preset position information of the first passage unit related to the non-contact reading part that read the user ID of the non-contact tag part of the movement support tool.

A movement support tool for a physically disabled person according to a second aspect is a movement support tool in a movement support system for a physically disabled person, such that the movement support system comprises: the movement support tool configured to support movement of a user in a passage; a plurality of passage units configured to be arranged side by side in the passage and operate to act on the movement support tool; and a control apparatus configured to be able to communicate with the movement support tool and control operations of the plurality of passage units. The movement support tool comprises: a magnetically attractive part configured to be attracted to a magnet; a non-contact tag part configured so that a user ID is embedded; a reception part configured to receive a wireless signal; an input part configured to be able to input destination information; an output part configured to be able to output a guidance; and a control part configured to control the reception part, the input part, and the output part. The magnetically attractive part is attracted to an electromagnet part of the passage unit. The user ID of the non-contact tag part is read by a non-contact reading part of the passage unit. The reception part receives the wireless signal transmitted from a transmission part of the passage unit. The control apparatus is configured to execute processing of acquiring the destination information and the user ID from the movement support tool. The control apparatus is configured to execute processing of acquiring the user ID of the non-contact tag part read by the non-contact reading part of a first passage unit closest to the movement support tool among the plurality of passage units, and preset position information of the first passage unit, from the first passage unit. The control apparatus is configured to execute processing of calculating a route from the position information of the first passage unit to the destination information. The control apparatus is configured to execute processings of: generating a guidance based on the route and the preset position information of the first passage unit related to the non-contact reading part that read the user ID of the non-contact tag part of the movement support tool; and outputting the generated guidance from the output part of the movement support tool through the transmission part of the first passage unit and the reception part of the movement support tool. The control apparatus is configured to execute processing of controlling each of the electromagnet parts of the plurality of passage units so as to attract (pull) the magnetically attractive part in a traveling direction of the route based on the route and the preset position information of the first passage unit related to the non-contact reading part that read the user ID of the non-contact tag part of the movement support tool.

A movement support method for a physically disabled person according to a third aspect is a movement support method for a physically disabled person, of supporting a movement of the physically disabled person, using a movement support system for the physically disabled person, such that the movement support system comprises: a movement support tool configured to support movement of a user in a passage; a plurality of passage units configured to be arranged side by side in the passage and operate to act on the movement support tool; and a control apparatus configured to be able to communicate with the movement support tool and control operations of the plurality of passage units, wherein the method comprises: inputting destination information into the movement support tool; notifying the destination information and a user ID from the movement support tool to the control apparatus; reading the user ID of the movement support tool by a first passage unit closest to the movement support tool among the plurality of passage units; notifying the user ID and preset position information of the first passage unit from the first passage unit to the control apparatus; calculating a route from the position information of the first passage unit to the destination information; generating a guidance based on the route and the preset position information of the first passage unit that read the user ID of the movement support tool; outputting the generated guidance from the movement support tool through the first passage unit; and controlling each of electromagnet parts of the plurality of passage units so as to attract (pull) the magnetically attractive part in a traveling direction of the route based on the route and the preset position information of the first passage unit that read the user ID of the movement support tool.

According to the first to third aspects, it is possible to contribute to navigating a physically disabled person to a destination safely, quickly, and without stalling.

PREFERRED MODES

Figure 1:
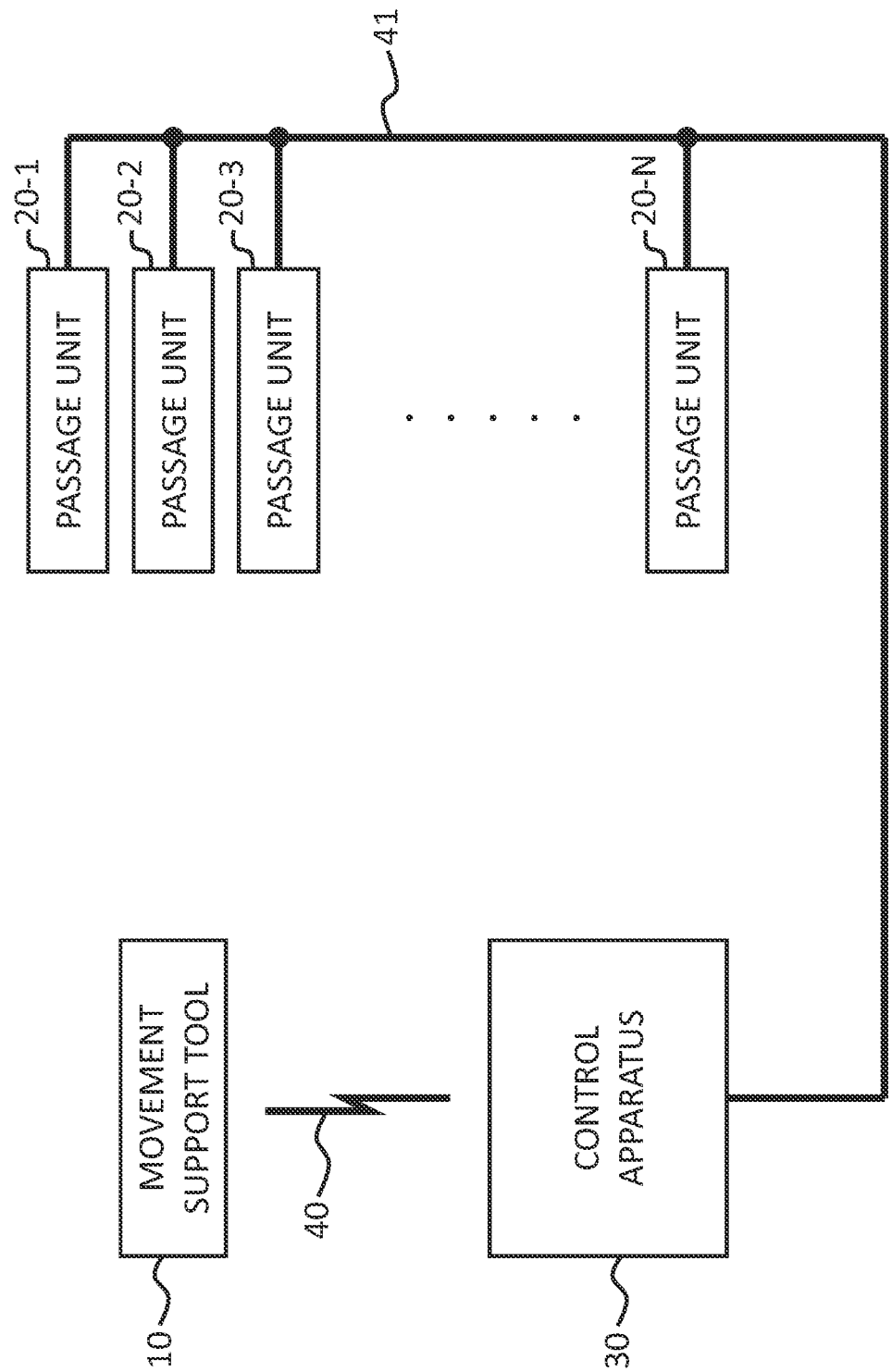
FIG. 1 is a block diagram schematically showing a configuration of a movement support system for a physically disabled person according to a first exemplary embodiment.

In the present disclosure described below, a movement support system for a physically disabled person according to Mode 1 and its modified mode(s) can be appropriately selected and combined.

As the movement support system for the physically disabled person according to Mode 1, it is possible to configure a movement support system for a physically disabled person, the movement support system comprising: a movement support tool configured to support movement of a user in a passage; a plurality of passage units configured to be arranged side by side in the passage and operate to act on the movement support tool: and a control apparatus configured to be able to communicate with the movement support tool and control operations of the plurality of passage units, wherein the movement support tool comprises: a magnetically attractive part configured to be attracted to a magnet; a non-contact tag part configured so that a user ID is embedded; a reception part configured to receive a wireless signal; an input part configured to be able to input destination information; an output part configured to be able to output a guidance; and a control part configured to control the reception part, the input part, and the output part, wherein the passage units comprise: an electromagnet part configured to be able to attract the magnetically attractive part; a non-contact reading part configured to be able to read the user ID from the non-contact tag part; a transmission part configured to be able to transmit the wireless signal to the reception part; and a control part configured to control the electromagnet part, the non-contact reading part and the transmission part, wherein the control apparatus is configured to execute processings of: acquiring the destination information and the user ID from the movement support tool; acquiring the user ID of the non-contact tag part read by the non-contact reading part of a first passage unit closest to the movement support tool among the plurality of passage units, and preset position information of the first passage unit, from the first passage unit; calculating a route from the position information of the first passage unit to the destination information; generating a guidance based on the route and the preset position information of the first passage unit related to the non-contact reading part that read the user ID of the non-contact tag part of the movement support tool; outputting the generated guidance from the output part of the movement support tool through the transmission part of the first passage unit and the reception part of the movement support tool; and controlling each of the electromagnet parts of the plurality of passage units so as to attract (pull) the magnetically attractive part in a traveling direction of the route based on the route and the preset position information of the first passage unit related to the non-contact reading part that read the user ID of the non-contact tag part of the movement support tool.

As a modified mode of the movement support system for the physically disabled person according to Mode 1, it is possible to configure the movement support system for the physically disabled person, such that the output part comprises an audio output part; and the guidance comprises voice information.

As a modification mode of the movement support system for the physically disabled person according to Mode 1, it is possible to configure the movement support system for the physically disabled person, such that the output part comprises a vibration output part; and the guidance comprises vibration pattern information.

As a modification mode of the movement support system for the physically disabled person according to Mode 1, it is possible to configure the movement support system for the physically disabled person, such that the magnetically attractive part is a permanent magnet; and in controlling each of the electromagnet parts of the plurality of passage units, the control part controls the electromagnet part of one passage unit next to the passage unit related to the non-contact reading part that read the user ID of the non-contact tag part of the movement support tool, to be turned on so that the facing surfaces of the electromagnet part and the permanent magnet have different polarities; and controls the electromagnet parts of the other passage units to be turned off.

As a modification mode of the movement support system for the physically disabled person according to Mode 1, it is possible to configure the movement support system for the physically disabled person, such that the magnetically attractive part is a ferromagnetic body; and in controlling each of the electromagnet parts of the plurality of passage units, the control part controls the electromagnet part of one passage unit next to the passage unit related to the non-contact reading part that read the user ID of the non-contact tag part of the movement support tool, to be turned on; and controls the electromagnet parts of the other passage units to be turned off.

As a modification mode of the movement support system for the physically disabled person according to Mode 1, it is possible to configure the movement support system for the physically disabled person, such that the magnetically attractive part is a permanent magnet; and in controlling each of the electromagnet parts of the plurality of passage units, the control part controls the electromagnet part of the passage unit related to the non-contact reading part that read the user ID of the non-contact tag part of the movement support tool, to be turned on so that the facing surfaces of the electromagnet part and the permanent magnet have the same polarity; controls the electromagnet part of one passage unit next to the passage unit to be turned on; and controls the electromagnet parts of the other passage units to be turned off.

As a modification mode of the movement support system for the physically disabled person according to Mode 1, it is possible to configure the movement support system for the physically disabled person, such that the movement support tool is a rod-shaped object; and the magnetically attractive part and the non-contact tag part are attached to a portion, close to the passage unit, in a main body of the movement support tool when the user holds the movement support tool.

As a modification mode of the movement support system for the physically disabled person according to Mode 1, it is possible to configure the movement support system for the physically disabled person, such that the movement support tool comprises a mobile robot part configured to be able to move on the passage units under control of the control part of the movement support tool.

In the present disclosure, as a movement support tool for a physically disabled person according to Mode 2, it is possible to configure a movement support tool in a movement support system for a physically disabled person, the movement support system comprising: the movement support tool configured to support movement of a user in a passage; a plurality of passage units configured to be arranged side by side in the passage and operate to act on the movement support tool; and a control apparatus configured to be able to communicate with the movement support tool and control operations of the plurality of passage units, wherein the movement support tool comprises: a magnetically attractive part configured to be attracted to a magnet; a non-contact tag part configured so that a user ID is embedded; a reception part configured to receive a wireless signal; an input part configured to be able to input destination information; an output part configured to be able to output a guidance; and a control part configured to control the reception part, the input part, and the output part, wherein the magnetically attractive part is attracted to an electromagnet part of the passage unit, wherein the user ID of the non-contact tag part is read by a non-contact reading part of the passage unit, wherein the reception part receives the wireless signal transmitted from a transmission part of the passage unit, and wherein the control apparatus is configured to execute processings of: acquiring the destination information and the user ID from the movement support tool; acquiring the user ID of the non-contact tag part read by the non-contact reading part of a first passage unit closest to the movement support tool among the plurality of passage units, and preset position information of the first passage unit, from the first passage unit; calculating a route from the position information of the first passage unit to the destination information; generating a guidance based on the route and the preset position information of the first passage unit related to the non-contact reading part that read the user ID of the non-contact tag part of the movement support tool; outputting the generated guidance from the output part of the movement support tool through the transmission part of the first passage unit and the reception part of the movement support tool; and controlling each of the electromagnet parts of the plurality of passage units so as to attract (pull) the magnetically attractive part in a traveling direction of the route based on the route and the preset position information of the first passage unit related to the non-contact reading part that read the user ID of the non-contact tag part of the movement support tool.

In the present disclosure, as a movement support method for a physically disabled person according to Mode 3, it is possible to configure a movement support method for a physically disabled person, of supporting a movement of the physically disabled person, using a movement support system for the physically disabled person, the movement support system comprising: a movement support tool configured to support movement of a user in a passage; a plurality of passage units configured to be arranged side by side in the passage and operate to act on the movement support tool; and a control apparatus configured to be able to communicate with the movement support tool and control operations of the plurality of passage units, wherein the method comprises: inputting destination information into the movement support tool; notifying the destination information and a user ID from the movement support tool to the control apparatus; reading the user ID of the movement support tool by a first passage unit closest to the movement support tool among the plurality of passage units; notifying the user ID and preset position information of the first passage unit from the first passage unit to the control apparatus; calculating a route from the position information of the first passage unit to the destination information; generating a guidance based on the route and the preset position information of the first passage unit that read the user ID of the movement support tool; outputting the generated guidance from the movement support tool through the first passage unit; and controlling each of electromagnet parts of the plurality of passage units so as to attract (pull) the magnetically attractive part in a traveling direction of the route based on the route and the preset position information of the first passage unit that read the user ID of the movement support tool.

Hereinafter, exemplary embodiments will be described with reference to drawings. When drawing-reference signs are attached in the present application, they are solely for the purpose of assisting understanding, and are not intended to be limited to the illustrated modes. Also, the following exemplary embodiments are merely examples, and do not limit the present invention. Further, connecting lines between blocks such as drawings referred to in the following description includes both bidirectional and unidirectional. A one-way arrow schematically shows a flow of a main signal (data), and does not exclude bidirectional. Furthermore, in circuit diagrams, block diagrams, internal configuration diagrams, connection diagrams, etc. shown in the disclosure of the present application, although explicit disclosure is omitted, an input port and an output port exist at the input end and the output end of each connection line, respectively. The same applies to the input/output interface. A program is executed via a computer apparatus, which comprises, for example, a processor, a storage device, an input device, a communication interface, and a display device as required, and the computer apparatus is configured to be able to communicate with inside device(s) or external apparatus(es) (including computer(s)) via a communication interface regardless of whether it is wired or wireless.

First Exemplary Embodiment

Figure 2:
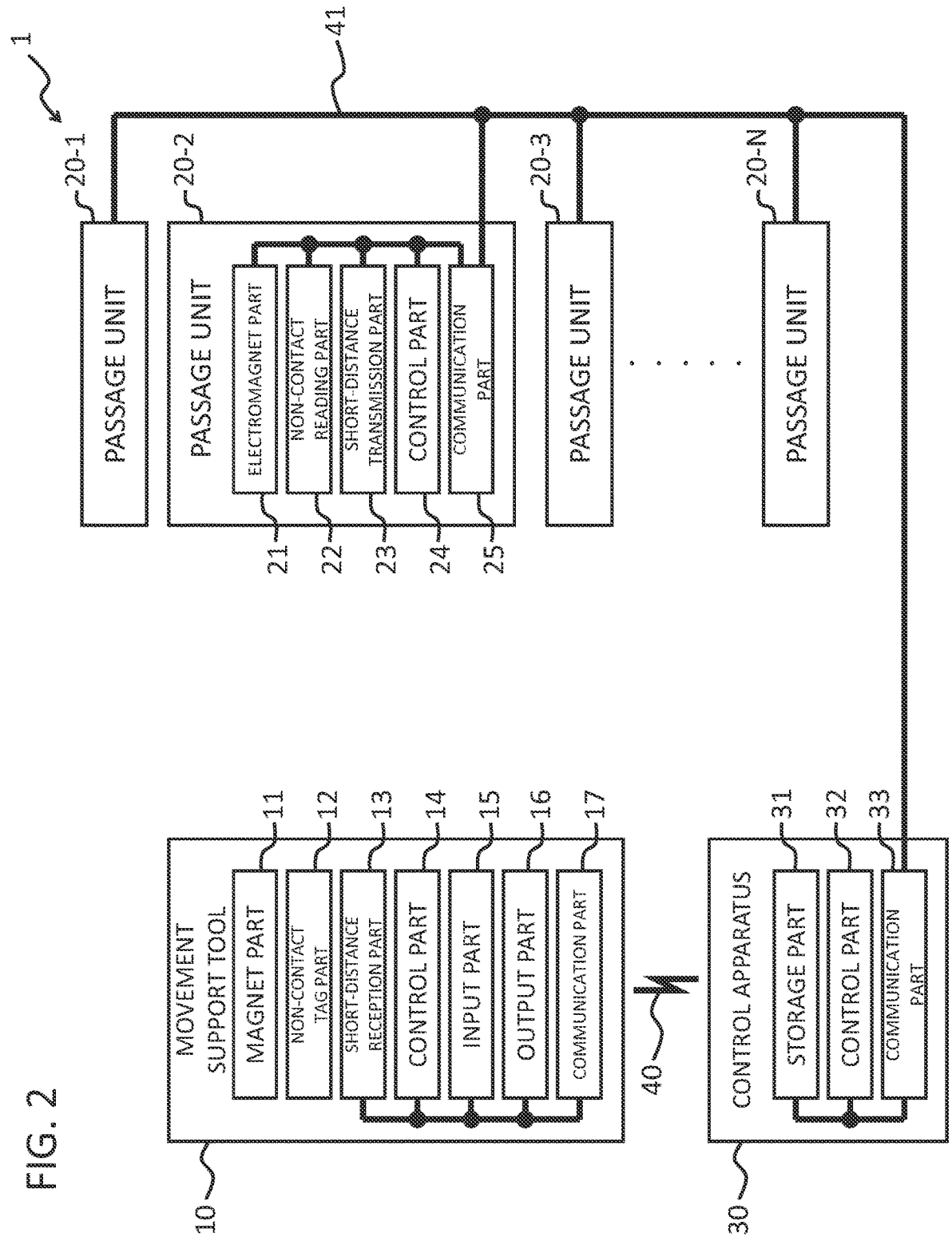
FIG. 2 is a block diagram schematically showing a detailed configuration of the movement support system for the physically disabled person according to the first exemplary embodiment.
Figure 3:
FIG. 3 is an image diagram schematically showing a configuration of a movement support tool in the movement support system for the physically disabled person according to the first exemplary embodiment.
Figure 4:
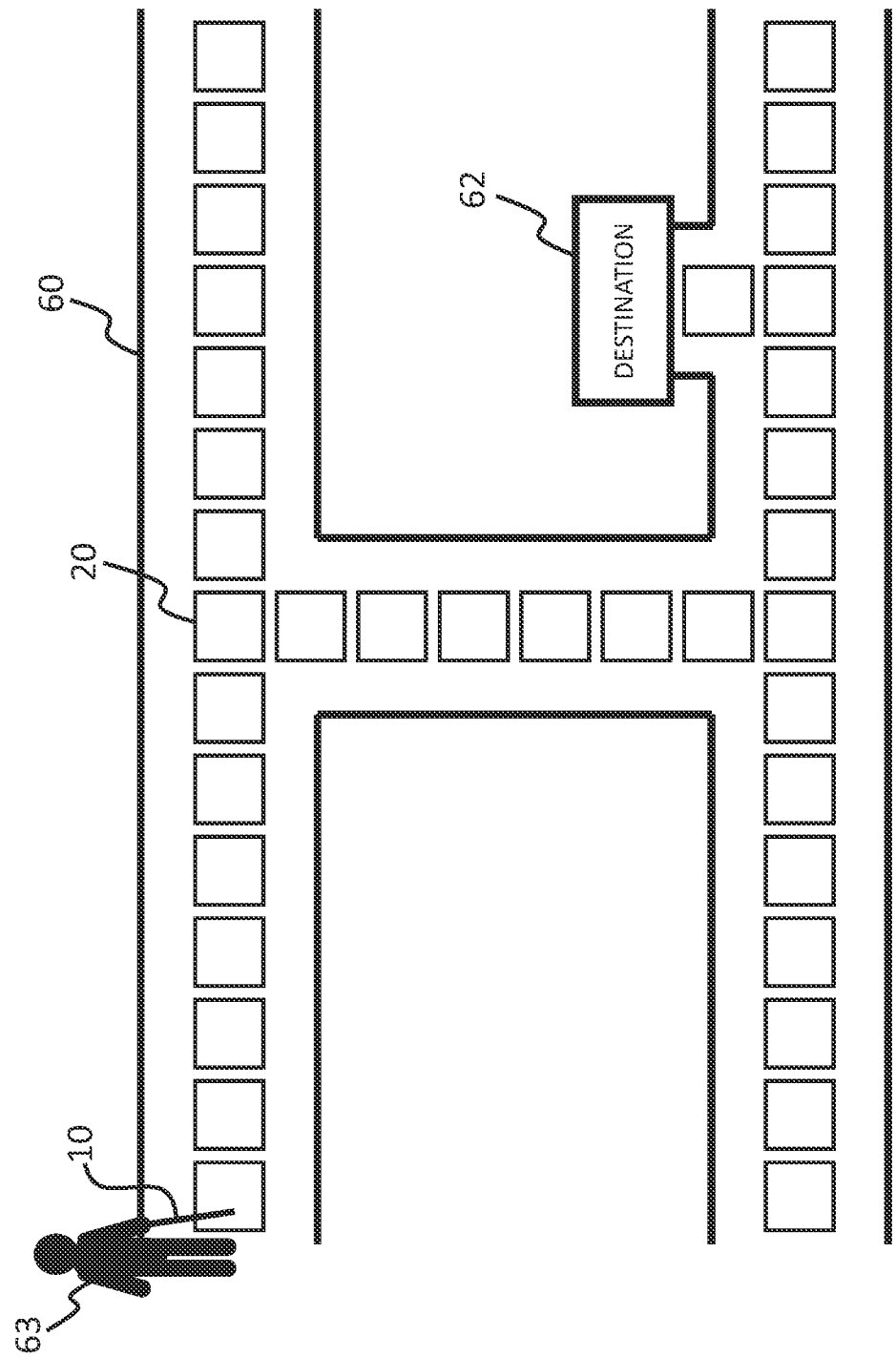
FIG. 4 is an image diagram schematically showing an arrangement of passage units in the movement support system for the physically disabled person according to the first exemplary embodiment.

A movement support system for a physically disabled person according to a first exemplary embodiment will be described with reference to drawings. FIG. 1 is a block diagram schematically showing a configuration of the movement support system for the physically disabled person according to the first exemplary embodiment. FIG. 2 is a block diagram schematically showing a detailed configuration of the movement support system for the physically disabled person according to the first exemplary embodiment. FIG. 3 is an image diagram schematically showing a configuration of a movement support tool in the movement support system for the physically disabled person according to the first exemplary embodiment. FIG. 4 is an image diagram schematically showing an arrangement of passage units in the movement support system for the physically disabled person according to the first exemplary embodiment.

The movement support system 1 for the physically disabled person is a system that supports a movement of the physically disabled person (user 63) in a passage 60 (see FIGS. 1, 2, and 4). The movement support system 1 for the physically disabled person can be used in areas such as city halls, stations, and airports, wherein the areas are highly public; have complicated facilities; and are strongly required to be barrier-free. The movement support system 1 for the physically disabled person comprises: a movement support tool 10; passage units 20-1 to 20-N; and a control apparatus 30.

The movement support tool 10 is a tool that supports the movement of the physically disabled person (here, a visually impaired person) as a user 63 (see FIGS. 1 to 4). As the movement support tool 10, for example, a rod-shaped object such as a cane or a wand can be used. The movement support tool 10 comprises: a magnet part 11; a non-contact tag part 12; a short-distance reception part 13; a control part 14; an input part 15; an output part 16; and a communication part 17.

The magnet part 11 is a part made of a permanent magnet (see FIGS. 2 and 3). As the permanent magnet of the magnet part 11, for example, an alnico magnet, a ferrite magnet, a neodymium magnet, a samarium cobalt magnet, or the like can be used. Instead of the magnet part 11, a ferromagnetic material such as iron, cobalt, nickel, or gadolinium may be used. The magnet part 11 is attached to a portion of the main body of the movement support tool 10, wherein the portion is close to the passage unit 20, when using the movement support tool 10. The magnet part 11 is attached to the main body of the movement support tool 10 so as to have a predetermined polarity (for example, N pole) on the passage unit 20 side. When generating a magnetic force having a polarity different from a polarity on the passage unit 20 side of the magnet part 11 on the upper side of the core of the electromagnet part 21 of the passage unit 20, the magnet part 11 is used in order to attract (pull) the magnet part 11 to the electromagnet part 21 of the passage unit 20 to generate a magnetic force.

The non-contact tag part 12 is a part made of a tag capable of reading embedded information by non-contact short-distance wireless communication (see FIGS. 2 and 3). As the non-contact tag part 12, for example, an RF (Radio Frequency) tag, an IC (Integrated Circuit) tag, an electronic tag, or the like can be used. A user ID (IDentifier) is embedded (stored) in the non-contact tag part 12. The non-contact tag part 12 is used, when the user 63 moves with the movement support tool 10 and enters a readable area of the non-contact reading part 22 of the passage unit 20 whose position is predetermined, in order to read the user ID embedded in the non-contact tag part 12 by the non-contact reading part 22 of the passage unit 20 and inform the control apparatus 30 of the position (corresponding to the position of the passage unit 20) of the user 63. The non-contact tag part 12 is attached to a portion in the main body of the movement support tool 10 when the user 63 holds the movement support tool 10, wherein the portion is close to the passage unit 20.

The short-distance reception part 13 is a function part that receives a short-distance wireless signal transmitted from the short-distance transmission part 23 of the passage unit 20 (see FIG. 2). As the short-distance reception part 13, for example, a receiver or a communication device capable of receiving an NFC (Near Field Communication) standard signal can be used. The short-distance reception part 13 is controlled by the control part 14.

The control part 14 is a function part that controls the short-distance reception part 13, the input part 15, the output part 16, and the communication part 17 (see FIG. 2). The control part 14 is electrically connected (or connected by bus) to the short-distance reception part 13, the input part 15, the output part 16, and the communication part 17. As the control part 14, for example, a unit such as a CPU (Central Processing Unit) or an MPU (Micro Processor Unit) can be used, and not only one unit but also a plurality of units may be used. The control part 14 controls the short-distance reception part 13 so as to cause the short-distance reception part 13 to receive the short-distance wireless signal transmitted from the short-distance transmission part 23 of the passage unit 20. The control part 14 controls the input part 15 to acquire information input from the input part 15. The control part 14 controls the output part 16 so as to cause the output part 16 to output information. The control part 14 controls the communication part 17 so as to cause the communication part 17 to transmit and receive information relative to control apparatus 30. The control part 14 performs predetermined information processing by executing a program(s).

The input part 15 is a function part that inputs information (see FIG. 2). As the input part 15, for example, a microphone, a touch panel, a button, or the like can be used. The input part 15 is controlled by the control part 14.

The output part 16 is a function part that outputs information (see FIG. 2). As the output part 16, for example, a speaker, a vibrator, a braille display, or the like can be used, and an information terminal or the like having an output part that is communicably connected via a communication part (not shown) may be used. The output part 16 is controlled by the control part 14.

The communication part 17 is a function part that communicates predetermined information, data, or signals relative to the control apparatus 30 (see FIG. 2). The communication part 17 is communicably connected to the control apparatus 30 via a wireless network 40 (for example, a mobile phone communication network or a mobile communication network). The communication part 17 is controlled by the control part 14.

The passage unit 20 (20-1 to 20-N) is a unit (hardware) that is arranged side by side (or buried, laid, or placed) in the passage 60 (for example, (walking path, stairs, slope, etc.)) (FIGS. 1, 2 and 4). The passage unit 20 (20-1 to 20-N) operates so as to act relative to the movement support tool 10. The positions of the passage units 20 (20-1 to 20-N) are predetermined. The passage units 20 (20-1 to 20-N) can be arranged side by side in a center of the passage 60 as shown in FIG. 4. Each of passage units 20 (20-1 to 20-N) comprises: an electromagnet part 21; a non-contact reading part 22; a short-distance transmission part 23; a control part 24; and a communication part 25.

The electromagnet part 21 is a function part that temporarily generates a magnetic force when energized (see FIG. 2). As the electromagnet part 21, for example, an electromagnet having a coil wound around a core of a magnetic material can be used. The electromagnet part 21 is arranged so as to generate polarity on the upper side. When the movement support tool 10 approaches the passage unit 20, the electromagnet part 21 is used in order to attract (pull) the magnet part 11 of the movement support tool 10 to the electromagnet part 21 by causing the upper side of the electromagnet part 21 to generate a magnetic force having a polarity different from a polarity on the passage unit 20 side of the magnet part 11 of the movement support tool 10. When the movement support tool 10 moves away from the passage unit 20, the electromagnet part 21 may be used in order to cause the upper side of the electromagnet part 21 to generate a magnetic force having the same polarity as a polarity on the passage unit 20 side of the magnet part 11 of the movement support tool 10 to press the magnet part 11 of the movement support tool 10 from the electromagnet part 21. The electromagnet part 21 is controlled by the control part 24.

The non-contact reading part (i.e., non-contact reader) 22 is a function part capable of reading information embedded in the non-contact tag part 12 of the movement support tool 10 by non-contact short-distance wireless communication (see FIGS. 2 and 3). As the non-contact reading part 22, for example, an RFID reader, an IC (Integrated Circuit) reader tag, or an electronic tag reader can be used. The non-contact reading part 22 is used in order to notify a position of the user 63 (corresponding to a position of the passage unit 20), when the user 63 is moving with the movement support tool 10, by reading the user ID from the non-contact tag part 12 of the movement support tool 10. It is used to inform the position of the unit 20). The non-contact reading part 22 is controlled by the control part 24.

The short-distance transmission part 23 is a function part that transmits a short-distance wireless signal (see FIG. 2). As the short-distance transmission part 23, for example, a transmitter or a communication device capable of transmitting an NFC (Near Field Communication) standard signal can be used. The short-distance wireless signal transmitted from the short-distance transmission part 23 can be received by the short-distance reception part 13 of the movement support tool 10. The short-distance transmission part 23 is controlled by the control part 24.

The control part 24 is a function part that controls the electromagnet part 21, the non-contact reading part 22, the short-distance transmission part 23, and the communication part 25 (see FIG. 2). The control part 24 is electrically connected (or connected by bus) to the electromagnet part 21, the non-contact reading part 22, the short-distance transmission part 23, and the communication part 25. As the control part 24, for example, a unit such as an MPU (Micro Processor Unit) or a CPU (Central Processing Unit) can be used, and not only one unit but also a plurality of units may be used. The control part 24 controls the electromagnet part 21 so as to cause the electromagnet part 21 to output a magnetic force. The control part 24 controls the non-contact reading part 22 so as to cause the non-contact reading part 22 to read the user ID from the non-contact tag part 12 of the movement support tool 10. The control part 24 controls the short-distance transmission part 23 so as to cause the short-distance transmission part 23 to transmit the short-distance wireless signal toward the short-distance reception part 13 of the movement support tool 10. The control part 24 controls the communication part 25 so as to cause to transmit and receive information relative to the movement support tool 10. The control part 24 performs predetermined information processing by executing a program(s).

The communication part 25 is a function part that communicates predetermined information, data, or signals relative to the control apparatus 30 (see FIG. 2). The communication part 25 is communicably connected to the control apparatus 30 via a wired network 41 (for example, a wired LAN (Local Area Network)). The communication part 25 is controlled by the control part 24.

The control apparatus 30 is an apparatus that controls the passage units 20 (20-1 to 20-N) (see FIGS. 1 and 2). The control apparatus 30 comprises: a storage part 31; a control part 32; and a communication part 33.

The storage part 31 is a function part that stores information such as data, a database, and a program (see FIG. 2). The storage part 31 inputs/outputs information and writes/reads data under control of the control part 32. The storage part 31 stores information related to surrounding environments (for example, positions of corners, stairs, slopes, escalators, elevators, etc.) according to each of the passage units 20 (20-1 to 20-N) as a database. The storage part 31 stores a program for calculating a route from a current location to a destination, a program for controlling ON/OFF of the electromagnet part 21 of each of the passage units 20 (20-1 to 20-N), and the like. As the storage part 31, for example, a RAM (Random Access Storage part), a hard disk device, an externally connected RAID (Redundant Arrays of Independent Disks) device, or the like can be used, and any storage device may be used.

The control part 32 is a function part that controls the storage part 31 and the communication part 33 (see FIG. 1). As the control part 32, for example, a unit such as a CPU (Central Processing Unit) or an MPU (Micro Processor Unit) can be used, and not only one unit but also a plurality of units may be used. The control part 32 is connected (or connected by bus) to the storage part 31 and the communication part 33. The control part 32 inputs/outputs information relative and writes/reads data to the storage part 31. The control part 32 controls the communication part 33 so as to cause the communication part 33 to transmit and receive information relative to the movement support tool 10 and each of the passage units 20 (20-1 to 20-N). The control part 32 reads a program stored in the storage part 31; loads the program into a main storage part; and executes the program, thereby, the control part 32 performs predetermined information processing(s).

The communication part 33 is a function part that communicates predetermined information, data, or signals relative to the movement support tool 10 and the passage units 20 (20-1 to 20-N) (see FIG. 2). The communication part 33 is communicably connected to the movement support tool 10 via the wireless network 40. The communication part 33 is communicably connected to each of the passage units 20 (20-1 to 20-N) via the wired network 41. The communication part 33 is controlled by the control part 32.

The program can be recorded on a computer-readable storage medium. The storage medium may be a non-transient such as a semiconductor memory, a hard disk, a magnetic recording medium, or an optical recording medium. Also, in the present disclosure, it is also possible to implement it as a computer program product. The program is input to a computer apparatus from an input device or from outside via a communication interface; is stored in a storage device; causes a processor to drive according to predetermined steps or processings; can cause to display processing results thereof, including an intermediate state via a display device step by step as necessary; or can cause to communicate with outside via a communication interface. The computer apparatus for that purpose typically comprises: for example, a processor; a storage device; an input device; a communication interface; and, if necessary, a display device, that can be connected to each other via a bus.

Figure 5:
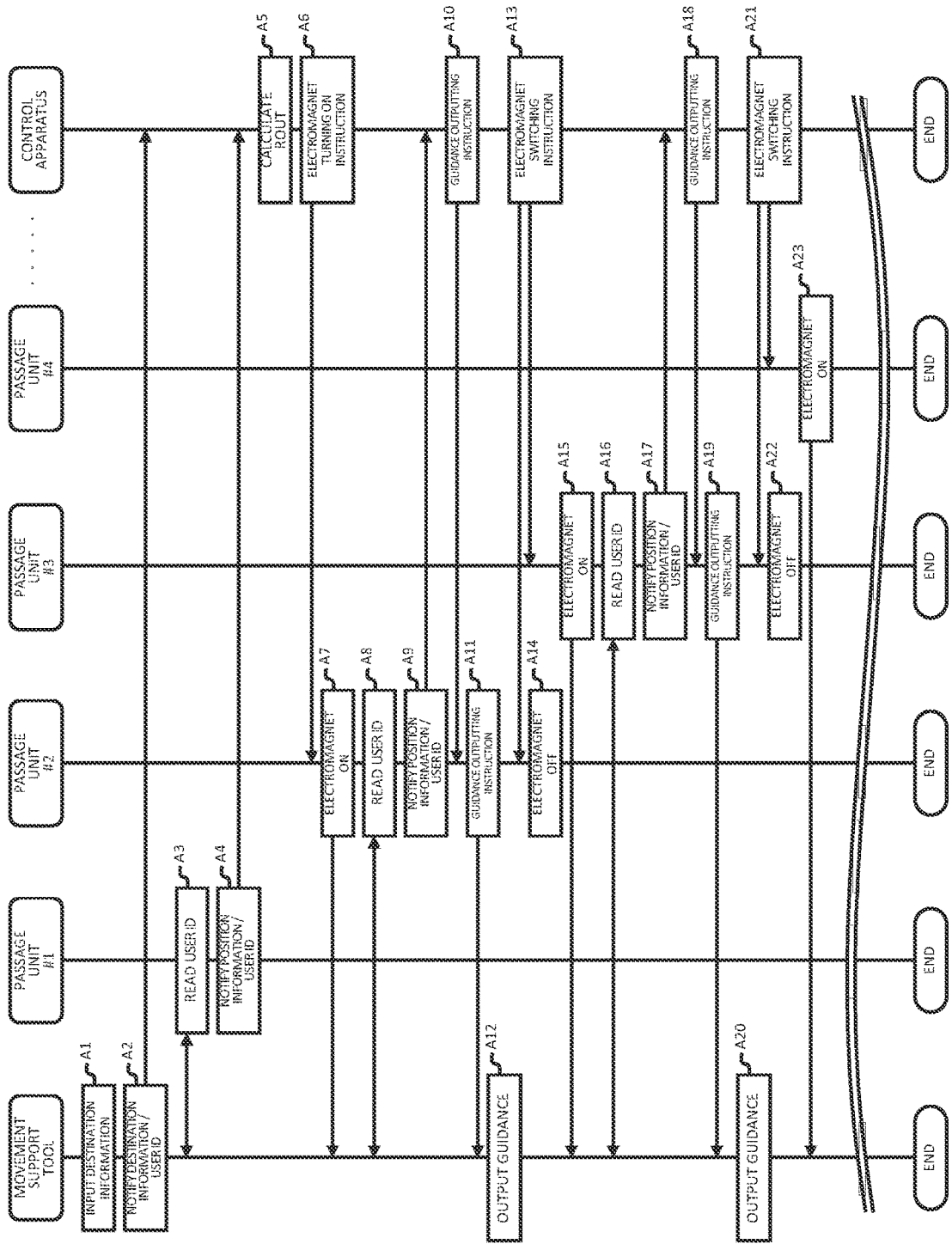
FIG. 5 is a flowchart schematically showing a part of operations of the movement support system for the physically disabled person according to the first exemplary embodiment.
Figure 6:
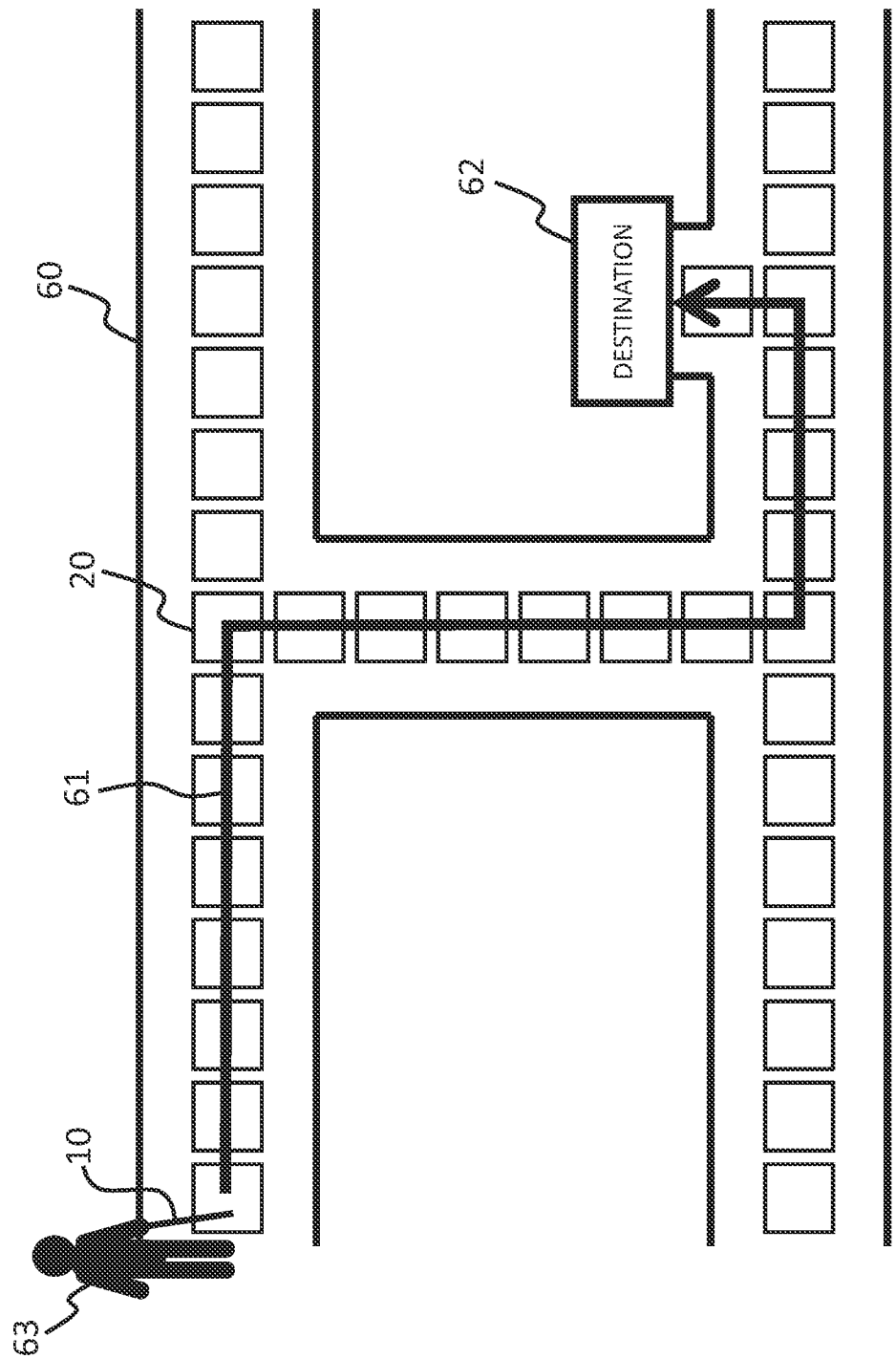
FIG. 6 is an image diagram when specifying a route from a position of a user to a destination in the movement support system for the physically disabled person according to the first exemplary embodiment.
Figure 7:
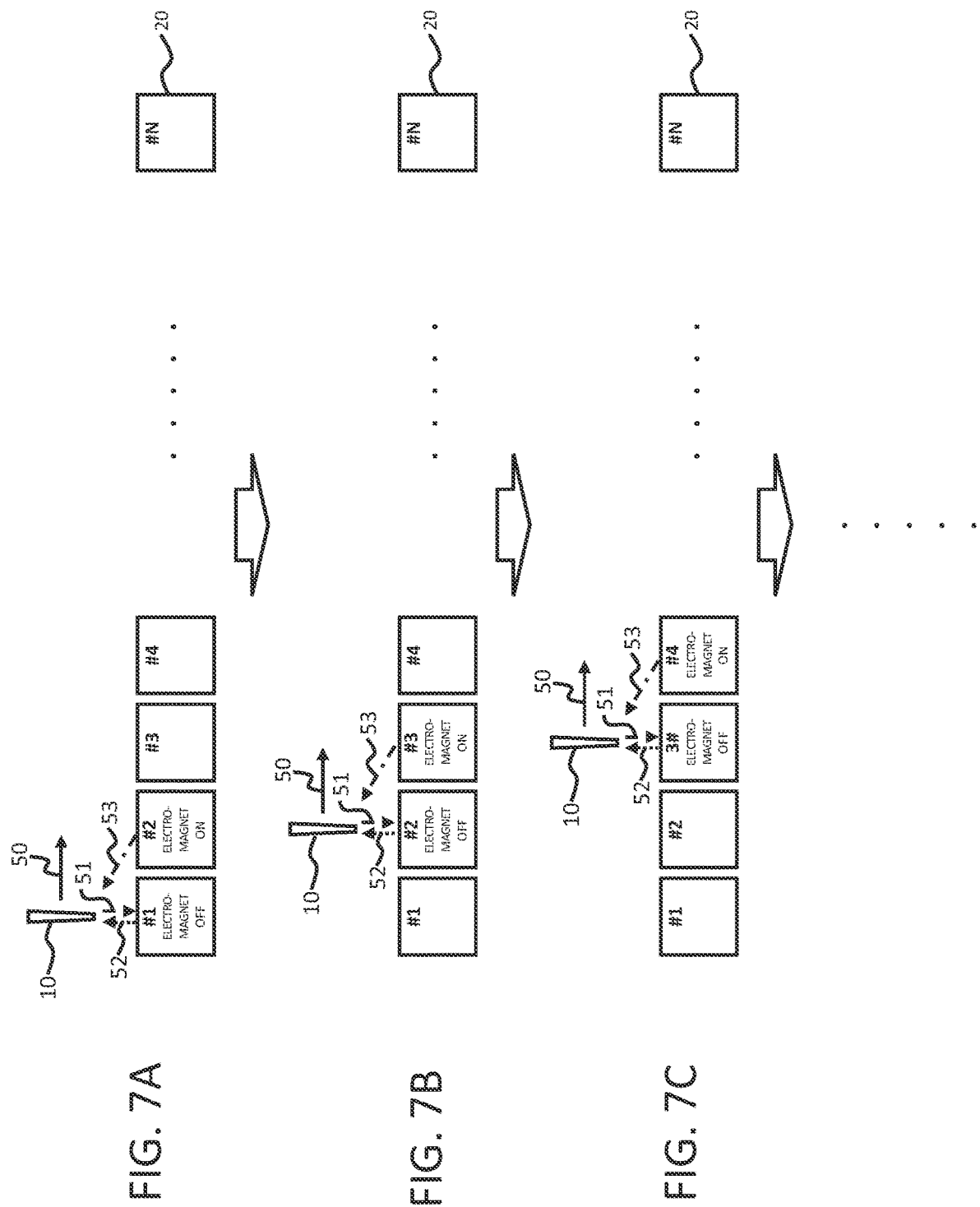
FIGS. 7A to 7C are image diagrams schematically showing transitions of operations of the passage units relative to movements of the movement support tool in the movement support system for the physically disabled person according to the first exemplary embodiment.

Operations of the movement support system for the physically disabled person according to the first exemplary embodiment will be described with reference to drawings. FIG. 5 is a flowchart schematically showing a part of operations of the movement support system for the physically disabled person according to the first exemplary embodiment. FIG. 6 is an image diagram when specifying a route from a position of a user to a destination in the movement support system for the physically disabled person according to the first exemplary embodiment. FIGS. 7A to 7C are image diagrams schematically showing transitions of operations of the passage units relative to movements of the movement support tool in the movement support system for the physically disabled person according to the first exemplary embodiment. Please refer to FIGS. 1 to 4 as to the configure of the movement support system for the physically disabled person.

First, the control part 14 of the movement support tool 10 receives input of destination information (for example, a toilet) from the input part 15 by an operation (for example, voice) of the user 63 (Step A1 in FIG. 5).

Next, the control part 14 of the movement support tool 10 notifies the control apparatus 30 of the input destination information and a preset unique user ID related to the movement support tool 10 through the communication part 17 (Step A2 in FIG. 5) As a result, the control apparatus 30 acquires the destination information and the user ID of the user 63. When the destination information is voice information, the control part 32 of the control apparatus 30 converts the voice into character data to recognize the destination information.

Next, the control part 24 of the passage unit 20 (passage unit #1 in FIG. 5) closest to the movement support tool 10 reads the user ID from the non-contact tag part 12 of the movement support tool 10 through the non-contact reading part 22. (Step A3 in FIG. 5).

Next, the control part 24 of the passage unit #1 notifies the control apparatus 30 of the user ID read in step A3 and the preset position information related to the passage unit #1 through the communication part 25 (Step A4 in FIG. 5). As a result, the control apparatus 30 acquires the position information (corresponding to the current location information of the user 63 at this time point) related to the passage unit #1 and the user ID.

Next, the control part 32 of the control apparatus 30 calculates a route (for example, the shortest route 61 as shown in FIG. 6) from the position of the passage unit #1 to the destination 62, based on the destination information corresponding to the acquired user ID and the position information related to the passage unit #1 (corresponding to the current location of the user 63 at this time point) (Step A5 in FIG. 5).

Next, based on the route calculated in step A5, the control part 32 of the control apparatus 30 performs an electromagnet turning on instruction to the passage unit #2 next to the passage unit #1 on the route to turn on the electromagnet (see FIG. 7A) (Step A6 in FIG. 5).

Next, the control part 24 of the passage unit #2 turns on the electromagnet part 21 so as to attract (pull) the magnet part 11 of the movement support tool 10 in response to the electromagnet turning on instruction from the control apparatus 30 (Step A7 in FIG. 5). As a result, the magnet part 11 of the movement support tool 10 is attracted (pulled) to the electromagnet part 21 of the passage unit #2.

Next, when the non-contact tag part 12 of the movement support tool 10 enters the readable area of the non-contact reading part 22 of the passage unit #2, the control part 24 of the passage unit #2 reads the user ID from the non-contact tag part 12 of the movement support tool 10 through the non-contact reading part 22 (step A8 in FIG. 5).

Next, the control part 24 of the passage unit #2 notifies the control apparatus 30 of the user ID read in Step A8 and the preset position information related to the passage unit #2 through the communication part 25 (Step A9 of FIG. 5). As a result, the control apparatus 30 acquires the position information (corresponding to the current location information of the user 63 at this time point) and the user ID related to the passage unit #2.

Next, based on the route calculated in step A5, the control part 32 of the control apparatus 30 generates a guidance for advancing to a position next to the position related to the passage unit #2 on the route and performs a guidance outputting instruction to the passage unit #2 so as to cause the movement support tool 10 to output the generated guidance (Step A10 in FIG. 5).

Here, the generated guidance may be a guidance for going straight if there is a straight passage, as to a position next to the position related to the passage unit #2 on the route; a guidance for turning to the right or left if there is a corner; or a guidance for notifying any of stairs, slopes, escalators, elevators, etc. if there is any of them. Also, the guidance can include distance information to the destination. Further, the guidance can be voice data or can be predetermined vibration pattern data.

Next, the control part 24 of the passage unit #2 performs a guidance outputting instruction to the movement support tool 10 through the short-distance transmission part 23 in response to the guidance outputting instruction from the control apparatus 30 (Step A11 in FIG. 5).

Next, the control part 14 of the movement support tool 10 receives the guidance outputting instruction from the passage unit #2 through the short-distance reception part 13 and outputs (outputs by voice or vibration) the guidance from the output part 16 in response to the guidance outputting instruction (Step A12 in FIG. 5).

Next, the control part 32 of the control apparatus 30 performs an electromagnet switching instruction to the passage unit #2 and the passage unit #3 through the communication part 25, based on the route calculated in Step A5, so as to turn off the electromagnet of the passage unit #2 on the route and turn on an electromagnet of the passage unit next to the passage unit #2 on the route (see FIG. 7B) (Step A13 in FIG. 5).

Next, the control part 24 of the passage unit #2 turns off the electromagnet part 21 so as to release the attraction (pull) of the magnet part 11 of the movement support tool 10 in response to the electromagnet switching instruction from the control apparatus 30. Step A14 in FIG. 5). As a result, the magnet part 11 of the movement support tool 10 becomes not attracted by the electromagnet part 21 of the passage unit #2.

Next, the control part 24 of the passage unit #3 turns on the electromagnet part 21 so as to attract (pull) the magnet part 11 of the movement support tool 10 in response to the electromagnet switching instruction from the control apparatus 30 (Step A15 in FIG. 5). As a result, the magnet part 11 of the movement support tool 10 is attracted to the electromagnet part 21 of the passage unit #3.

Next, when the non-contact tag part 12 of the movement support tool 10 enters a readable area of the non-contact reading part 22 of the passage unit #3, the control part 24 of the passage unit #3 reads the user ID from the non-contact tag part 12 of the movement support tool 10 through the non-contact reading part 22 (Step A16 in FIG. 5).

Next, the control part 24 of the passage unit #3 notifies the control apparatus 30 of the user ID read in step A16 and the preset position information related to the passage unit #3 through the communication part 25 (FIG. FIG. Step 5 A17). As a result, the control apparatus 30 acquires the position information (corresponding to the current location information of the user 63 at this time point) and the user ID related to the passage unit #3.

Next, the control part 32 of the control apparatus 30 generates a guidance for advancing to a position next to the position related to the passage unit #3 on the route based on the route calculated in Step A5 and performs a guidance outputting instruction to the passage unit #3 so as to cause the movement support tool 10 to output the generated guidance (step A18 in FIG. 5).

Next, the control part 24 of the passage unit #3 performs the guidance outputting instruction to the movement support tool 10 through the short-distance transmission part 23 in response to the guidance outputting instruction from the control apparatus 30 (Step A19 in FIG. 5).

Next, the control part 14 of the movement support tool 10 receives the guidance outputting instruction from the passage unit #3 through the short-distance reception part 13 and outputs (outputs by voice or vibration) the guidance from the output part 16 in response to the guidance outputting instruction (Step A20 in FIG. 5).

Next, based on the calculated route, the control part 32 of the control apparatus 30 performs an electromagnet switching instruction to the passage unit #3 and the passage unit #4 through the communication part 25 so as to turn off the electromagnet of the passage unit #3 and turn on an electromagnet of the passage unit #4 next to the passage unit #3 (see FIG. 7C) (Step A21 in FIG. 5).

Next, the control part 24 of the passage unit #3 turns off the electromagnet part 21 so as to release the attraction (pull) of the magnet part 11 of the movement support tool 10 in response to the electromagnet switching instruction from the control apparatus 30 (Step A22 in FIG. 5). As a result, the magnet part 11 of the movement support tool 10 becomes not attracted (pulled) by the electromagnet part 21 of the passage unit #3.

Next, the control part 24 of the passage unit #4 turns on the electromagnet part 21 so as to attract(pull) the magnet part 11 of the movement support tool 10 in response to the electromagnet switching instruction from the control apparatus 30 (Step A23 in FIG. 5). As a result, the magnet part 11 of the movement support tool 10 is attracted (pulled) to the electromagnet part 21 of the passage unit #4.

According to the first exemplary embodiment, by guiding the user 63 as the physically disabled person using the output part 16 while controlling the ON/OFF of the electromagnet part 21 of each of the passage units 20 to attract (pull) the magnet part 11 of the movement support tool 10, it is possible to contribute to navigating a physically disabled person to a destination safely, quickly, and without stalling. Also, according to the first exemplary embodiment, since a guidance is generated in response to a route from a current location to a destination, it is possible to dynamically provide information to the user 63. Also, according to the first exemplary embodiment, even in a place to be visited for a first time, since the user 63 is attracted (pulled) by the magnetic force to a destination designated by the user 63, it is possible to obtain a reaching force to a destination similarly to a healthy person. Further, according to the first exemplary embodiment, by controlling so that only the electromagnet part 21 of the passage unit 20 immediately before a traveling direction of the user 63 is turned on, it is possible to suppress interference with others. Furthermore, according to the first exemplary embodiment, by determining the user 63 by the user ID, the person to be guided can be identified, and mistakes with others can be prevented.

Second Exemplary Embodiment

Figure 8:
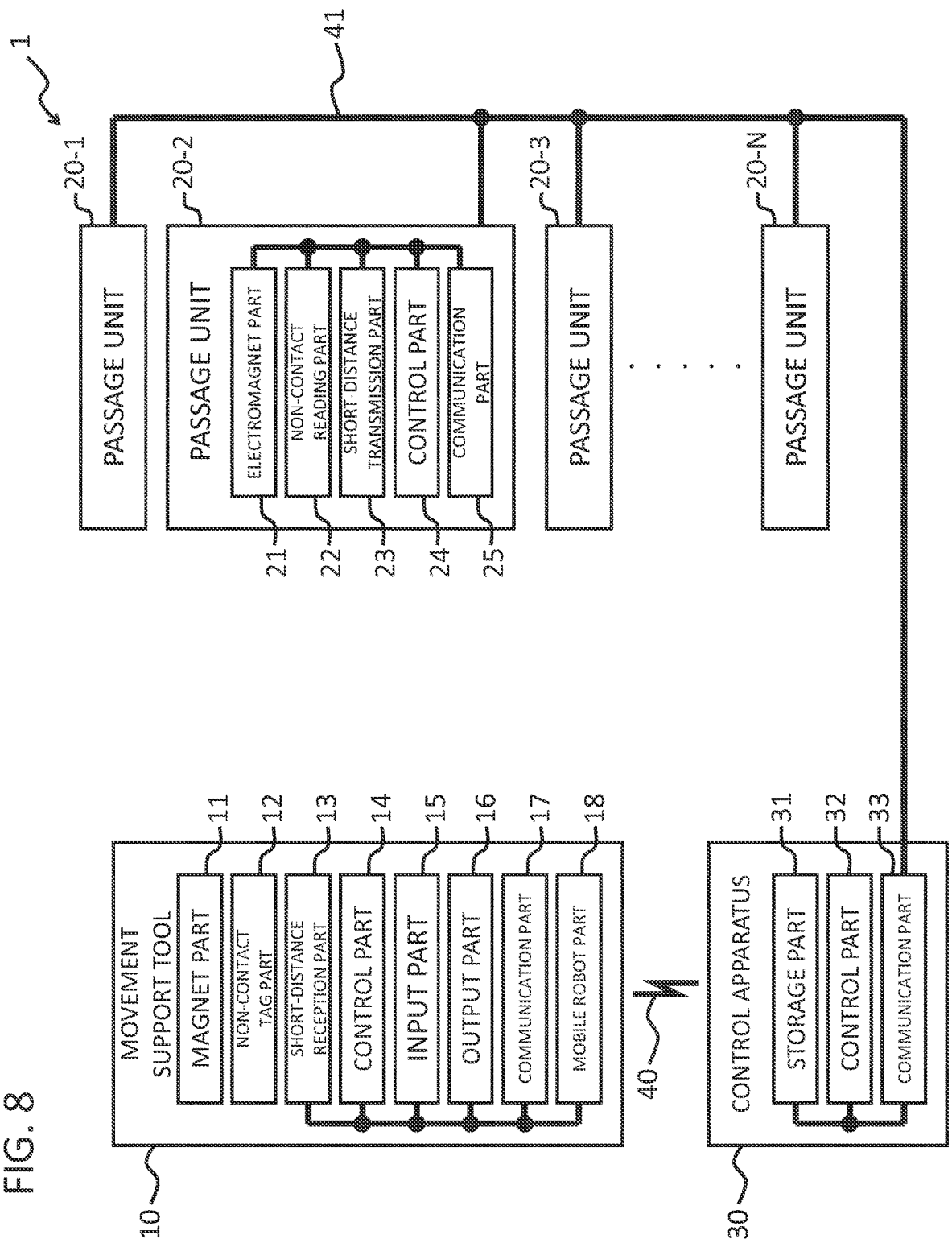
FIG. 8 is a block diagram schematically showing a configuration of a movement support system for a physically disabled person according to a second exemplary embodiment.

A movement support system for a physically disabled person according to a second exemplary embodiment will be described with reference to a drawing. FIG. 8 is a block diagram schematically showing a configuration of the movement support system for the physically disabled person according to the second exemplary embodiment.

The second exemplary embodiment is a modification of the first exemplary embodiment, and let a form of the movement support tool 10 be a form of a robot such as a miniature car, a dog-shaped robot, and a humanoid robot capable of moving the movement support tool 10 on the passage unit 20 (20-1 to 20-N), a mobile robot part 18 is added as a configuration part for realizing the robot (see FIG. 8). The mobile robot part 18 may be configured to be able to move by driving a plurality of wheels (not shown) and may be configured to be able to control and move a plurality of legs having a joint(s). The mobile robot part 18 is controlled by the control part 14. Other configurations and operations are the same as those in the first exemplary embodiment.

According to the second exemplary embodiment, similarly to the first exemplary embodiment, it is possible to contribute to navigating a physically disabled person to a destination safely, quickly, and without stalling and by adding the mobile robot part 18 in the movement support tool 10, it is possible to realize a sense of security and walking speed in which a physically disabled person is attracted (pulled, towed) by a person or a guide dog.

Third Exemplary Embodiment

Figure 9:
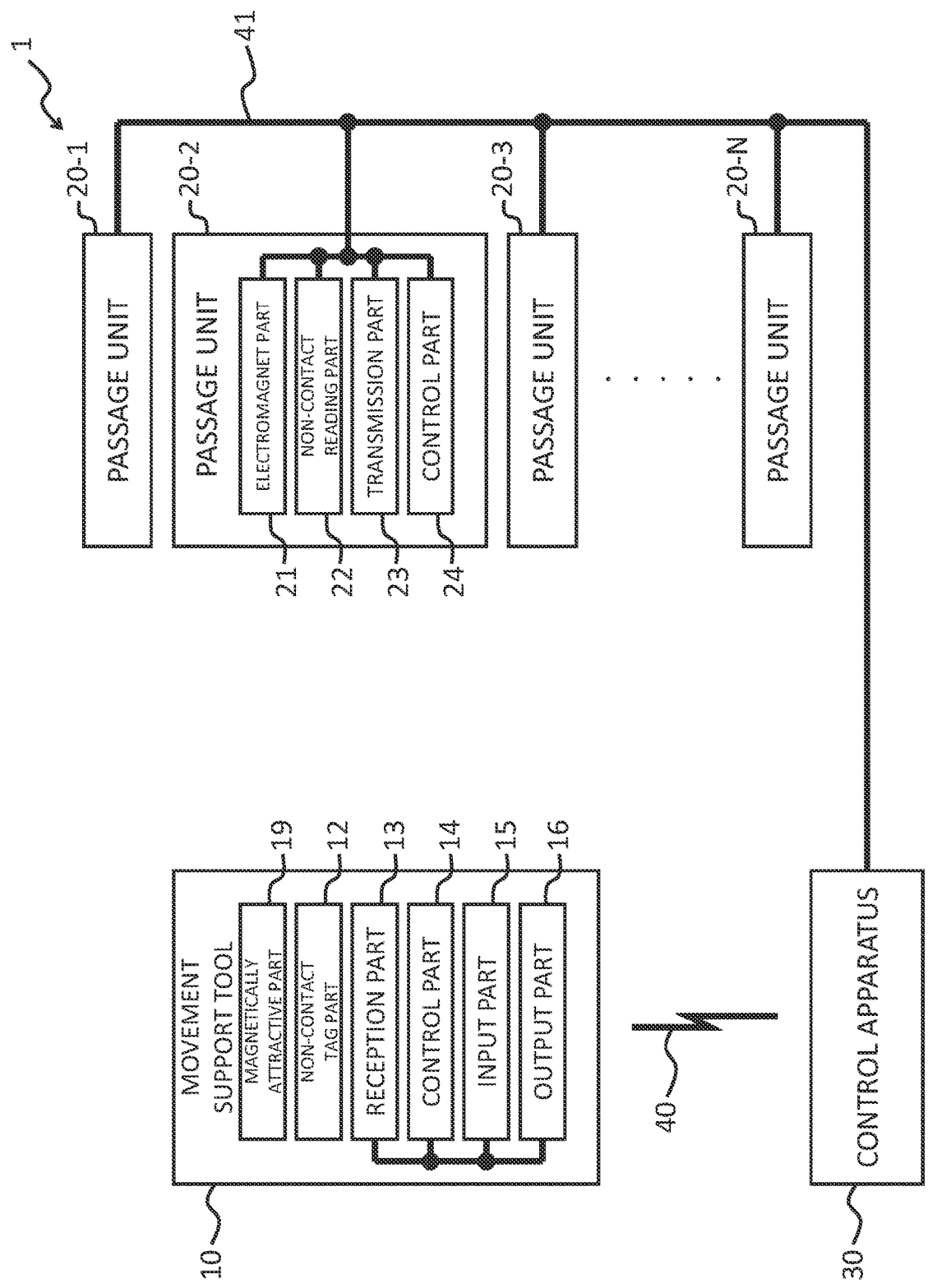
FIG. 9 is a block diagram schematically showing a configuration of a movement support system for a physically disabled person according to a third exemplary embodiment.

A movement support system for a physically disabled person according to a third exemplary embodiment will be described with reference to a drawing. FIG. 9 is a block diagram schematically showing a configuration of the movement support system for the physically disabled person according to the third exemplary embodiment.

The movement support system 1 for the physically disabled person is a system that supports a movement of the physically disabled person in a passage (see FIG. 9). The movement support system 1 for the physically disabled person comprises: a movement support tool 10; a plurality of passage units 20 (20-1 to 20-N); and a control apparatus 30.

The movement support tool 10 is a tool that is configured to support movement of a user in a passage. The movement support tool 10 comprises: a magnetically attractive part 19 configured to be attracted to a magnet; a non-contact tag part 12 configured so that a user ID is embedded; a reception part 13 configured to receive a wireless signal; an input part 15 configured to be able to input destination information; an output part 16 configured to be able to output a guidance; and a control part 14 configured to control the reception part 13, the input part 15, and the output part 16.

The passage units 20 are units (hardware) that are configured to be arranged side by side in the passage and operate to act on the movement support tool 10. The passage unit 20 (each) comprises: an electromagnet part 21 configured to be able to attract the magnetically attractive part 19; a non-contact reading part 22 configured to be able to read the user ID from the non-contact tag part 12; a transmission part 23 configured to be able to transmit the wireless signal to the reception part 13; and a control part 24 configured to control the electromagnet part 21, the non-contact reading part 22 and the transmission part 23.

The control apparatus 30 is an apparatus that is configured to be able to communicate with the movement support tool 10 and control operations of the plurality of passage units 20. The control apparatus 30 is configured to execute a processing of acquiring the destination information and the user ID from the movement support tool 10. The control apparatus 30 is configured to execute a processing of acquiring the user ID of the non-contact tag part 12 read by the non-contact reading part 22 of a first passage unit 20 closest to the movement support tool 10 among the plurality of passage units 20, and preset position information of the first passage unit 20, from the first passage unit 20. The control apparatus 30 is configured to execute a processing of calculating a route from the position information of the first passage unit 20 to the destination information. The control apparatus 30 is configured to execute processings of generating a guidance based on the route and the preset position information of the first passage unit 20 related to the non-contact reading part 22 that read the user ID of the non-contact tag part 12 of the movement support tool 10; and outputting the generated guidance from the output part 16 of the movement support tool 10 through the transmission part 23 of the first passage unit 20 and the reception part 13 of the movement support tool 10. The control apparatus 30 is configured to execute a processing of controlling each of the electromagnet parts 21 of the plurality of passage units 20 so as to attract (pull) the magnetically attractive part 19 of the movement support tool 10 in a traveling direction of the route based on the route and the preset position information of the first passage unit 20 related to the non-contact reading part 22 that read the user ID of the non-contact tag part 12 of the movement support tool 10.

According to the third exemplary embodiment, each of electromagnet parts 21 of the plurality of passage units 20 is controlled so as to attract (pull) the magnetically attractive part 19 of the movement support tool 10 in a traveling direction of the route, and the guidance is output from the output part 16 of the movement support tool 10, thereby, it is possible to contribute to navigating a physically disabled person to a destination safely, quickly, and without stalling.

Figure 10:
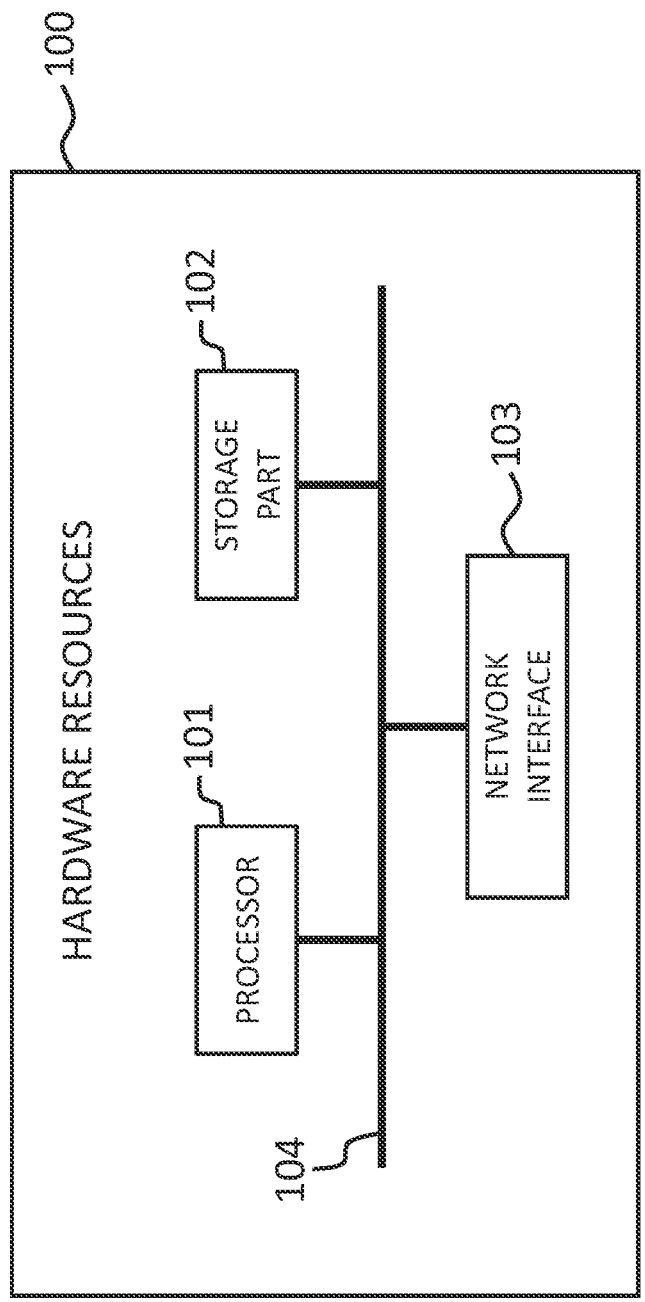
FIG. 10 is a block diagram schematically showing a configuration of hardware resources.

The control apparatus according to the first to third exemplary embodiments can be configured by so-called hardware resources (information processing apparatus, computer), and one comprising a configuration exemplarily shown in FIG. 10 can be used. For example, the hardware resources 100 comprises: a processor 101; a storage part 102; a network interface 103; and the like, which are connected to each other by an internal bus 104.

Note that the configuration shown in FIG. 10 is not intended to limit a hardware configuration of the hardware resources 100. The hardware resources 100 may comprise hardware (for example, an input/output interface) (not shown). Alternatively, the number of units such as the processor 101 comprised in the hardware resources 100 is not limited to the example shown in FIG. 10, and for example, a plurality of processors 101 may be comprised in an apparatus. As the processor 101, for example, a CPU (Central Processing part), an MPU (Micro Processor Unit), or the like can be used.

As the storage part 102, for example, RAM (Random Access Storage part), ROM (Read Only Storage part), HDD (Hard Disk Drive), SSD (Solid State Drive), or the like can be used.

As the network interface 103, for example, a LAN (Local Area Network) card, a network adapter, a network interface card, or the like can be used.

Functions of the hardware resources 100 are realized by the above-mentioned processing module. For example, the processing module is realized by the processor 101 executing a program stored in the storage part 102. Also, the program can be updated by downloading the program via a network or using a storage medium in which the program is stored. Further, the processing module may be realized by a semiconductor chip. That is, functions performed by the processing module may be realized by executing software on some hardware.

Part or all of the above exemplary embodiments may be described as the following MODEs, but is not limited to the following.

[Mode 1]
A movement support system for a physically disabled person, comprising:
a movement support tool configured to support movement of a user in a passage;
a plurality of passage units configured to be arranged side by side in the passage and operate to act on the movement support tool: and a control apparatus configured to be able to communicate with the movement support tool and control operations of the plurality of passage units,
 wherein the movement support tool comprises:
  a magnetically attractive part configured to be attracted to a magnet;
  a non-contact tag part configured so that a user ID is embedded;
  a reception part configured to receive a wireless signal;
  an input part configured to be able to input destination information;
  an output part configured to be able to output a guidance; and
  a control part configured to control the reception part, the input part, and the output part,
 wherein the passage units comprise:
  an electromagnet part configured to be able to attract the magnetically attractive part;
  a non-contact reading part configured to be able to read the user ID from the non-contact tag part;
  a transmission part configured to be able to transmit the wireless signal to the reception part; and
  a control part configured to control the electromagnet part, the non-contact reading part and the transmission part,
 wherein the control apparatus is configured to execute processings of: acquiring the destination information and the user ID from the movement support tool;
  acquiring the user ID of the non-contact tag part read by the non-contact reading part of a first passage unit closest to the movement support tool among the plurality of passage units, and preset position information of the first passage unit, from the first passage unit;
  calculating a route from the position information of the first passage unit to the destination information;
  generating a guidance based on the route and the preset position information of the first passage unit related to the non-contact reading part that read the user ID of the non-contact tag part of the movement support tool;
  outputting the generated guidance from the output part of the movement support tool through the transmission part of the first passage unit and the reception part of the movement support tool; and
  controlling each of the electromagnet parts of the plurality of passage units so as to attract (pull) the magnetically attractive part of the movement support tool in a traveling direction of the route based on the route and the preset position information of the first passage unit related to the non-contact reading part that read the user ID of the non-contact tag part of the movement support tool.

[Mode 2]
The movement support system for the physically disabled person according to MODE 1, wherein
the output part comprises an audio output part; and
the guidance comprises voice information.

[Mode 3]
The movement support system for the physically disabled person according to MODE 1 or 2, wherein
the output part comprises a vibration output part; and
the guidance comprises vibration pattern information.

[Mode 4]
The movement support system for the physically disabled person according to any one of MODEs 1 to 3, wherein
the magnetically attractive part is a permanent magnet; and
in controlling each of the electromagnet parts of the plurality of passage units, the control part controls the electromagnet part of one passage unit next to the passage unit related to the non-contact reading part that read the user ID of the non-contact tag part of the movement support tool, to be turned on so that the facing surfaces of the electromagnet part and the permanent magnet have different polarities; and controls the electromagnet parts of the other passage units to be turned off.

[Mode 5]
The movement support system for the physically disabled person according to any one of MODEs 1 to 3, wherein
the magnetically attractive part is a ferromagnetic body; and
in controlling each of the electromagnet parts of the plurality of passage units, the control part controls the electromagnet part of one passage unit next to the passage unit related to the non-contact reading part that read the user ID of the non-contact tag part of the movement support tool, to be turned on; and controls the electromagnet parts of the other passage units to be turned off.

[Mode 6]
The movement support system for the physically disabled person according to any one of MODEs 1 to 3, wherein
the magnetically attractive part is a permanent magnet; and
in controlling each of the electromagnet parts of the plurality of passage units, the control part controls the electromagnet part of the passage unit related to the non-contact reading part that read the user ID of the non-contact tag part of the movement support tool, to be turned on so that the facing surfaces of the electromagnet part and the permanent magnet have the same polarity; controls the electromagnet part of one passage unit next to the passage unit to be turned on; and controls the electromagnet parts of the other passage units to be turned off.

[Mode 7]
The movement support system for the physically disabled person according to any one of MODEs 1 to 6, wherein
the movement support tool is a rod-shaped object; and
the magnetically attractive part and the non-contact tag part are attached to a portion, close to the passage unit, in a main body of the movement support tool when the user holds the movement support tool.

[Mode 8]
The movement support system for the physically disabled person according to any one of MODEs 1 to 6, wherein the movement support tool comprises a mobile robot part configured to be able to move on the passage units under control of the control part of the movement support tool.

[Mode 9]
A movement support tool in a movement support system for a physically disabled person, the movement support system comprising:
the movement support tool configured to support movement of a user in a passage;
a plurality of passage units configured to be arranged side by side in the passage and operate to act on the movement support tool; and
a control apparatus configured to be able to communicate with the movement support tool and control operations of the plurality of passage units,
wherein the movement support tool comprises:
  a magnetically attractive part configured to be attracted to a magnet;
  a non-contact tag part configured so that a user ID is embedded;
  a reception part configured to receive a wireless signal;
  an input part configured to be able to input destination information;
  an output part configured to be able to output a guidance; and
  a control part configured to control the reception part, the input part, and the output part,
wherein the magnetically attractive part is attracted to an electromagnet part of the passage unit,
wherein the user ID of the non-contact tag part is read by a non-contact reading part of the passage unit,
wherein the reception part receives the wireless signal transmitted from a transmission part of the passage unit, and
wherein the control apparatus is configured to execute processings of: acquiring the destination information and the user ID from the movement support tool;
  acquiring the user ID of the non-contact tag part read by the non-contact reading part of a first passage unit closest to the movement support tool among the plurality of passage units, and preset position information of the first passage unit, from the first passage unit;
  calculating a route from the position information of the first passage unit to the destination information;
  generating a guidance based on the route and the preset position information of the first passage unit related to the non-contact reading part that read the user ID of the non-contact tag part of the movement support tool;
  outputting the generated guidance from the output part of the movement support tool through the transmission part of the first passage unit and the reception part of the movement support tool; and
  controlling each of the electromagnet parts of the plurality of passage units so as to attract (pull) the magnetically attractive part in a traveling direction of the route based on the route and the preset position information of the first passage unit related to the non-contact reading part that read the user ID of the non-contact tag part of the movement support tool.

[Mode 10]
A movement support method for a physically disabled person, of supporting a movement of the physically disabled person, using a movement support system for the physically disabled person, the movement support system comprising:
  a movement support tool configured to support movement of a user in a passage;
  a plurality of passage units configured to be arranged side by side in the passage and operate to act on the movement support tool; and
  a control apparatus configured to be able to communicate with the movement support tool and control operations of the plurality of passage units,
wherein the method comprises:
  inputting destination information into the movement support tool; notifying the destination information and a user ID from the movement support tool to the control apparatus;

reading the user ID of the movement support tool by a first passage unit closest to the movement support tool among the plurality of passage units;

notifying the user ID and preset position information of the first passage unit from the first passage unit to the control apparatus;

calculating a route from the position information of the first passage unit to the destination information;

generating a guidance based on the route and the preset position information of the first passage unit that read the user ID of the movement support tool;

outputting the generated guidance from the movement support tool through the first passage unit; and controlling each of electromagnet parts of the plurality of passage units so as to attract (pull) the magnetically attractive part in a traveling direction of the route based on the route and the preset position information of the first passage unit that read the user ID of the movement support tool.

It should be noted that each disclosure of the above PTLs and NPLs shall be incorporated herein by citation. Within a framework of the entire disclosure of the present invention (including claims and drawings), it is possible to modify or adjust the exemplary embodiments or examples further based on the basic technical concept thereof. Also, within the framework of entire disclosure of the present invention, various combinations or selections (non-selection if necessary) of various disclosed elements (including each element of each claim, each element of each exemplary embodiment or example, each element of each drawing, etc.) is possible. That is, it goes without saying that the present invention includes various deformations and modifications that can be made by one skilled in the art in accordance with all disclosures including claims and drawings, and the technical concept. Further, as to the numerical values and numerical ranges described in the present application, it is considered that arbitrary intermediate values, lower numerical values, and small ranges are described even if not explicitly recited.

REFERENCE SIGNS LIST

1 Movement support system for physically disabled person
10 Movement support tool
11 Magnet part
12 Non-contact tag part
13 Short-distance reception part (reception part)
14 Control part
15 Input part
16 Output part
17 Communication part
18 Mobile robot part
19 Magnetically attractive part
20, 20-1 to 20-N Passage unit
21 Electromagnet part
22 Non-contact reading part
23 Short-distance transmission part (transmission part)
24 Control part
25 Communication part
30 Control apparatus
31 Storage part
32 Control part
33 Communication part
40 Wireless network
41 Wired network
50 Movement direction
51 Radio wave
52 Short-distance wireless signal
53 Magnetism
60 Passage
61 Route
62 Destination
63 User
100 Hardware resources
101 Processor
102 Storage part
103 Network interface
104 Internal bus

What is claimed is:

1. A movement support system for a physically disabled person, comprising:

a movement support tool configured to support movement of a user in a passage;

a plurality of passage units configured to be arranged side by side in the passage and operate to act on the movement support tool; and a control apparatus configured to be able to communicate with the movement support tool and control operations of the plurality of passage units;

wherein the movement support tool comprises:

a magnetically attractive part configured to be attracted to a magnet;

a non-contact tag part configured so that a user ID is embedded;

a reception part configured to receive a wireless signal;

an input part configured to be able to input destination information;

an output part configured to be able to output a guidance; and a control part configured to control the reception part, the input part, and the output part;

wherein the passage units comprise:

an electromagnet part configured to be able to attract the magnetically attractive part;

a non-contact reading part configured to be able to read the user ID from the non-contact tag part;

a transmission part configured to be able to transmit the wireless signal to the reception part; and a control part configured to control the electromagnet part, the non-contact reading part and the transmission part;

wherein the control apparatus is configured to execute processings of:

acquiring the destination information and the user ID from the movement support tool;

acquiring the user ID of the non-contact tag part read by the non-contact reading part of a first passage unit closest to the movement support tool among the plurality of passage units, and preset position information of the first passage unit, from the first passage unit;

calculating a route from the position information of the first passage unit to the destination information;

generating a guidance based on the route and the preset position information of the first passage unit related to the non-contact reading part that read the user ID of the non-contact tag part of the movement support tool;

outputting the generated guidance from the output part of the movement support tool through the transmission part of the first passage unit and the reception part of the movement support tool; and controlling each of the electromagnet parts of the plurality of passage units so as to attract (pull) the magnetically attractive part of the movement support tool in a traveling direction of the route based on the route and the preset position information of the first passage unit related to the non-contact reading part that read the user ID of the non-contact tag part of the movement support tool.

2. The movement support system for the physically disabled person according to claim 1, wherein
the output part comprises an audio output part; and
the guidance comprises voice information.

3. The movement support system for the physically disabled person according to claim 2, wherein
the output part comprises a vibration output part; and
the guidance comprises vibration pattern information.

4. The movement support system for the physically disabled person according to claim 3, wherein
the magnetically attractive part is a permanent magnet; and
in controlling each of the electromagnet parts of the plurality of passage units, the control part controls the electromagnet part of one passage unit next to the passage unit related to the non-contact reading part that read the user ID of the non-contact tag part of the movement support tool, to be turned on so that the facing surfaces of the electromagnet part and the permanent magnet have different polarities; and controls the electromagnet parts of the other passage units to be turned off.

5. The movement support system for the physically disabled person according to claim 3, wherein
the magnetically attractive part is a ferromagnetic body; and
in controlling each of the electromagnet parts of the plurality of passage units, the control part controls the electromagnet part of one passage unit next to the passage unit related to the non-contact reading part that read the user ID of the non-contact tag part of the movement support tool, to be turned on; and controls the electromagnet parts of the other passage units to be turned off.

6. The movement support system for the physically disabled person according to claim 3, wherein
the magnetically attractive part is a permanent magnet; and
in controlling each of the electromagnet parts of the plurality of passage units, the control part controls the electromagnet part of the passage unit related to the non-contact reading part that read the user ID of the non-contact tag part of the movement support tool, to be turned on so that the facing surfaces of the electromagnet part and the permanent magnet have the same polarity; controls the electromagnet part of one passage unit next to the passage unit to be turned on; and controls the electromagnet parts of the other passage units to be turned off.

7. The movement support system for the physically disabled person according to claim 2, wherein
the magnetically attractive part is a permanent magnet; and
in controlling each of the electromagnet parts of the plurality of passage units, the control part controls the electromagnet part of one passage unit next to the passage unit related to the non-contact reading part that read the user ID of the non-contact tag part of the movement support tool, to be turned on so that the facing surfaces of the electromagnet part and the permanent magnet have different polarities; and controls the electromagnet parts of the other passage units to be turned off.

8. The movement support system for the physically disabled person according to claim 2, wherein
the magnetically attractive part is a ferromagnetic body; and
in controlling each of the electromagnet parts of the plurality of passage units, the control part controls the electromagnet part of one passage unit next to the passage unit related to the non-contact reading part that read the user ID of the non-contact tag part of the movement support tool, to be turned on; and controls the electromagnet parts of the other passage units to be turned off.

9. The movement support system for the physically disabled person according to claim 2, wherein
the magnetically attractive part is a permanent magnet; and
in controlling each of the electromagnet parts of the plurality of passage units, the control part controls the electromagnet part of the passage unit related to the non-contact reading part that read the user ID of the non-contact tag part of the movement support tool, to be turned on so that the facing surfaces of the electromagnet part and the permanent magnet have the same polarity; controls the electromagnet part of one passage unit next to the passage unit to be turned on; and controls the electromagnet parts of the other passage units to be turned off.

10. The movement support system for the physically disabled person according to claim 1, wherein
the output part comprises a vibration output part; and
the guidance comprises vibration pattern information.

11. The movement support system for the physically disabled person according to claim 10, wherein
the magnetically attractive part is a permanent magnet; and
in controlling each of the electromagnet parts of the plurality of passage units, the control part controls the electromagnet part of one passage unit next to the passage unit related to the non-contact reading part that read the user ID of the non-contact tag part of the movement support tool, to be turned on so that the facing surfaces of the electromagnet part and the permanent magnet have different polarities; and controls the electromagnet parts of the other passage units to be turned off.

12. The movement support system for the physically disabled person according to claim 10, wherein
the magnetically attractive part is a ferromagnetic body; and
in controlling each of the electromagnet parts of the plurality of passage units, the control part controls the electromagnet part of one passage unit next to the passage unit related to the non-contact reading part that read the user ID of the non-contact tag part of the movement support tool, to be turned on; and controls the electromagnet parts of the other passage units to be turned off.

13. The movement support system for the physically disabled person according to claim 10, wherein
the magnetically attractive part is a permanent magnet; and
in controlling each of the electromagnet parts of the plurality of passage units, the control part controls the electromagnet part of the passage unit related to the non-contact reading part that read the user ID of the non-contact tag part of the movement support tool, to be turned on so that the facing surfaces of the electromagnet part and the permanent magnet have the same polarity; controls the electromagnet part of one passage unit next to the passage unit to be turned on; and controls the electromagnet parts of the other passage units to be turned off.

14. The movement support system for the physically disabled person according to claim 1, wherein
the magnetically attractive part is a permanent magnet; and
in controlling each of the electromagnet parts of the plurality of passage units, the control part controls the electromagnet part of one passage unit next to the passage unit related to the non-contact reading part that read the user ID of the non-contact tag part of the movement support tool, to be turned on so that the facing surfaces of the electromagnet part and the permanent magnet have different polarities; and controls the electromagnet parts of the other passage units to be turned off.

15. The movement support system for the physically disabled person according to claim 1, wherein
the magnetically attractive part is a ferromagnetic body; and
in controlling each of the electromagnet parts of the plurality of passage units, the control part controls the electromagnet part of one passage unit next to the passage unit related to the non-contact reading part that read the user ID of the non-contact tag part of the movement support tool, to be turned on; and controls the electromagnet parts of the other passage units to be turned off.

16. The movement support system for the physically disabled person according to claim 1, wherein
the magnetically attractive part is a permanent magnet; and
in controlling each of the electromagnet parts of the plurality of passage units, the control part controls the electromagnet part of the passage unit related to the non-contact reading part that read the user ID of the non-contact tag part of the movement support tool, to be turned on so that the facing surfaces of the electromagnet part and the permanent magnet have the same polarity; controls the electromagnet part of one passage unit next to the passage unit to be turned on; and controls the electromagnet parts of the other passage units to be turned off.

17. The movement support system for the physically disabled person according to claim 1, wherein
the movement support tool is a rod-shaped object; and
the magnetically attractive part and the non-contact tag part are attached to a portion, close to the passage unit, in a main body of the movement support tool when the user holds the movement support tool.

18. The movement support system for the physically disabled person according to claim 1, wherein the movement support tool comprises a mobile robot part configured to be able to move on the passage units under control of the control part of the movement support tool.

19. A movement support tool in a movement support system for a physically disabled person, the movement support system comprising:
the movement support tool configured to support movement of a user in a passage;
a plurality of passage units configured to be arranged side by side in the passage and operate to act on the movement support tool; and
a control apparatus configured to be able to communicate with the movement support tool and control operations of the plurality of passage units;
wherein the movement support tool comprises:
a magnetically attractive part configured to be attracted to a magnet;
a non-contact tag part configured so that a user ID is embedded;
a reception part configured to receive a wireless signal;
an input part configured to be able to input destination information;
an output part configured to be able to output a guidance; and
a control part configured to control the reception part, the input part, and the output part;
wherein the magnetically attractive part is attracted to an electromagnet part of the passage unit;
wherein the user ID of the non-contact tag part is read by a non-contact reading part of the passage unit;
wherein the reception part receives the wireless signal transmitted from a transmission part of the passage unit; and
wherein the control apparatus is configured to execute processings of:
acquiring the destination information and the user ID from the movement support tool;
acquiring the user ID of the non-contact tag part read by the non-contact reading part of a first passage unit closest to the movement support tool among the plurality of passage units, and preset position information of the first passage unit, from the first passage unit;
calculating a route from the position information of the first passage unit to the destination information;
generating a guidance based on the route and the preset position information of the first passage unit related to the non-contact reading part that read the user ID of the non-contact tag part of the movement support tool;
outputting the generated guidance from the output part of the movement support tool through the transmission part of the first passage unit and the reception part of the movement support tool; and
controlling each of the electromagnet parts of the plurality of passage units so as to attract (pull) the magnetically attractive part in a traveling direction of the route based on the route and the preset position information of the first passage unit related to the non-contact reading part that read the user ID of the non-contact tag part of the movement support tool.

20. A movement support method for a physically disabled person, of supporting a movement of the physically disabled person, using a movement support system for the physically disabled person, the movement support system comprising:
a movement support tool configured to support movement of a user in a passage;
a plurality of passage units configured to be arranged side by side in the passage and operate to act on the movement support tool; and
a control apparatus configured to be able to communicate with the movement support tool and control operations of the plurality of passage units;
wherein the movement support method comprises:
inputting destination information into the movement support tool;
notifying the destination information and a user ID from the movement support tool to the control apparatus;

reading the user ID of the movement support tool by a first passage unit closest to the movement support tool among the plurality of passage units;
notifying the user ID and preset position information of the first passage unit from the first passage unit to the control apparatus;
calculating a route from the position information of the first passage unit to the destination information;
generating a guidance based on the route and the preset position information of the first passage unit that read the user ID of the movement support tool;
outputting the generated guidance from the movement support tool through the first passage unit; and
controlling each of electromagnet parts of the plurality of passage units so as to attract (pull) the magnetically attractive part in a traveling direction of the route based on the route and the preset position information of the first passage unit that read the user ID of the movement support tool.

\* \* \* \* \*